US005321160A

United States Patent [19]

Hironaka et al.

[11] Patent Number: 5,321,160
[45] Date of Patent: Jun. 14, 1994

[54] PROCESS FOR PRODUCING AN ETHYLENAMINE

[75] Inventors: Toshio Hironaka, Tokuyama; Noritaka Nagasaki; Yasushi Hara, both of Shinnanyo, all of Japan

[73] Assignee: Tosoh Corporation, Shinnanyo, Japan

[21] Appl. No.: 921,204

[22] Filed: Jul. 29, 1992

[30] Foreign Application Priority Data

| Jul. 31, 1991 | [JP] | Japan | 3-213095 |
| Jul. 31, 1991 | [JP] | Japan | 3-213096 |
| Sep. 13, 1991 | [JP] | Japan | 3-261243 |
| Sep. 13, 1991 | [JP] | Japan | 3-261244 |

[51] Int. Cl.$^5$ .......................................... C07C 209/16
[52] U.S. Cl. ................................. 564/480; 544/358; 544/402
[58] Field of Search ........................................ 564/480

[56] References Cited

U.S. PATENT DOCUMENTS

| B 391,828 | 4/1976 | Boettger et al. | 252/454 |
| 3,151,115 | 9/1964 | Moss et al. | 260/268 |
| 4,234,458 | 11/1980 | Antos | 252/441 |
| 4,625,030 | 11/1986 | Best | 564/480 |
| 4,647,701 | 3/1987 | Gibson | 564/480 |
| 4,977,266 | 12/1990 | Burgess et al. | 564/480 |
| 5,073,635 | 12/1991 | Bowman et al. | 564/480 |

FOREIGN PATENT DOCUMENTS

| 0002630 | 6/1979 | European Pat. Off. . |
| 0197611 | 10/1986 | European Pat. Off. . |
| 0476578 | 3/1992 | European Pat. Off. . |
| 53-038716 | 10/1978 | Japan . |
| 1569714 | 6/1980 | United Kingdom . |

Primary Examiner—Glennon H. Hollran
Assistant Examiner—Scott C. Rand
Attorney, Agent, or Firm—Oblon, Spivak, McClelland, Maier & Neustadt

[57] ABSTRACT

A process for producing an ethylenamine, which comprises reacting ammonia and/or an ethylenamine with an ethanolamine in the presence of hydrogen to obtain an ethylenamine having an increased number of ethylene chains over the ammonia and/or the ethylenamine used as the starting material, wherein a catalyst comprising Ni, X and M elements wherein X is Re, Ir, Pt or Pd, and when X is Re, Ir or Pb, M is at least one rare earth element selected from the group consisting of scandium, yttrium, praseodymium, neodymium, samarium, europium, gadolinium, terbium, dysprosium, holmium, erbium, thulium, ytterbium and lutetium, and when X is Pd, M is at least one member selected from the group consisting of rare earth elements is used for the reaction.

11 Claims, No Drawings

PROCESS FOR PRODUCING AN ETHYLENAMINE

The present invention relates to a process for producing an ethylenamine. More particularly, it relates to a process for producing an ethylenamine, which is characterized by the use of a catalyst comprising Ni, X and M elements, wherein X is Re, Ir, Pt or Pd, and when X is Re, Ir or Pt, M is at least one rare earth element selected from the group consisting of scandium, yttrium, praseodymium, neodymium, samarium, europium, gadolinium, terbium, dysprosium, holmium, erbium, thulium, ytterbium and lutetium, and when X is Pd, M is at least one member selected from the group consisting of rare earth elements. Ethylenamines are aliphatic amine compounds useful for e.g. agricultural chemicals, chelating agents, epoxy-curing agents, wet paper strength-increasing agents or additives for lubricant oils.

As a conventional process for producing ethylenamines, a process is known wherein ethylene dichloride is used as a starting material and is reacted with ammonia. This process is widely used, and it is thereby possible to produce an ethylenamine of industrially useful quality containing no substantial cyclic products However, this process has a problem that a large amount of sodium chloride is formed as by-product, and its separation and treatment are costly. As a process which is free from the by-product, a process is widely employed wherein a monoethanolamine is used as a starting material and is reacted with ammonia in the presence of hydrogen This process is characterized by the use of a catalyst, and various catalysts have been proposed.

Conventional catalysts include, for example, Ni +Cu Cr (U.S. Pat. No. 3,151,115), Ni +Fe (U.S. Pat. No. 3,766184), Ni +Cu (Japanese Unexamined Patent Publication No. 88892/1979), Ni +Co +Cu (U.S. Pat. No. 4,014,933) and Ni +Re (Japanese Unexamined Patent Publication No. 108534/1981). All of these catalysts contain Ni and have second and third components incorporated to improve the performance of the catalysts. However, with these catalysts, cyclic products such as piperazine and amines containing hydroxyl groups will be formed in substantial amounts. Thus, they are not satisfactory from the viewpoint of selectivity. Further, they are not industrially satisfactory also from the viewpoint of the catalytic activities.

As described above, many catalysts have been disclosed for a process for producing ethylenamines using monoethanolamine free from the by-product. However, such catalysts have low activities and can not be regarded as industrially satisfactory catalysts, since cyclic products and hydroxyl group-containing amines are produced in substantial amounts.

Thus, it has been desired to develop a process for producing an ethylenamine using a high performance catalyst having the catalytic activity and selectivity substantially improved over the conventional Ni-type catalysts.

Under these circumstances, the present inventors have conducted extensive studies on processes for producing ethylenamines and as a result, have found a new fact that when at least one member selected from the group consisting of scandium, yttrium, praseodymium, neodymium, samarium, europium, gadolinium, terbium, dysprosium, holmium, erbium, thulium, ytterbium and lutetium, is added to nickel (Ni) together with rhenium (Re), iridium (Ir) or platinum (Pt), the catalytic activity and selectivity will be improved over a case where such a member is added to Ni without adding Re, Ir or Pt, or over a case of Ni-Re, Ni-Ir or Ni-Pt without addition of such a member; and that when at least one member selected from the group consisting of rare earth elements is added to Ni together with palladium (Pd), the catalyst activity and selectivity will be improved over a case where such a member is added to Ni without adding Pd, or over a case of Ni-Pd without addition of such a member The present invention has been accomplished on the basis of these discoveries.

Thus, the present invention provides a process for producing an ethylenamine, which comprises reacting ammonia and/or an ethylenamine with an ethanolamine in the presence of hydrogen to obtain an ethylenamine having an increased number of ethylene chains over the ammonia and/or the ethylenamine used as the starting material, wherein a catalyst comprising Ni, X and M elements wherein X is Re, Ir, Pt or Rd, and when X is Re, Ir or Pt, M is at least one rare earth element selected from the group consisting of scandium, yttrium, praseodymium, neodymium, samarium, europium, gadolinium, terbium, dysprosium, holmium, erbium, thulium, ytterbium and lutetium and when X is Pd, M is at least one member selected from the group consisting of rare earth elements, is used for the reaction.

Now, the present invention will be described in detail with reference to the preferred embodiments.

The catalyst to be used in the process of the present invention includes four types of catalyst systems i.e. Ni-M-Re, Ni-M-Ir, Ni-M-Pt and Ni-M-Pd, wherein M is as defined above.

In the process of the present invention, Ni, M, Re, Ir, Pt and Pd mean compounds containing the respective metal elements or single substances of the respective metal elements. The respective metal elements may take various states.

For example, Ni includes nickel metal, nickel oxide, nickel hydroxide, a nickel salt, a nickel alkoxide and a nickel complex Among them, nickel metal and nickel oxide are preferred which are stable under the reaction conditions.

M includes a metal, an oxide, a hydroxide, a salt, an alkoxide and a complex Specifically, it includes, for example, scandium oxide, yttrium metal, yttrium oxide, yttrium hydroxide, an yttrium salt, lanthanum metal, lanthanum oxide, cerium metal, cerium oxide, a cerium salt, praseodymium oxide, a praseodymium salt, neodymium oxide, samarium oxide, europium oxide, an europium salt, gadolinium oxide, terbium metal, terbium oxide, holmium metal, dysprosium oxide, holmium metal, holmium oxide, erbium metal, erbium oxide, thulium oxide, ytterbium metal, ytterbium oxide, an ytterbium salt, lutetium metal and lutetium oxide. Among them, metals and oxides are preferred which are stable under the reaction conditions.

Likewise, Re, Ir, Pt and Pd include the respective metals, oxides and salts. Among them metals and oxides are preferred which are stable under the reaction conditions.

In the process of the present invention, the catalyst components are used usually as supported on a carrier to improve the catalytic activity However, they may not necessarily be supported on a carrier When supported on a carrier, there may be employed as the carrier a metal oxide such as silica, alumina, titania, zirconia, magnesia, calcia, thoria, niobium oxide or zinc oxide, a mixed oxide such as silica-calcia, silica-magnesia, silica-alumina, zeolite, pumice, diatomaceous earth or acid clay, silicon carbide, porous glass, or active carbon. Some carriers have an interaction with the metal elements. Those having a strong interaction may have a chemical bond between the carriers and the metal elements, whereby the activities, selectivity, heat resistance or catalyst life may change. When the metal elements are to be supported on a carrier, they may simultaneously be supported, or they may separately be supported. There is no particular restriction as to the supporting method. The following methods may be mentioned, for example:

1) a method which is usually called an impregnation method, wherein a solution of the metal elements is impregnated to a carrier.

2) a method which is usually called a coprecipitation method, wherein a solution of the metal elements and a solution having the carrier components dissolved therein are mixed, and a precipitation agent is added thereto for decomposition.

3) a method which is usually called a precipitation method, wherein a carrier is immersed in a solution of the metal elements, and then adding a precipitation agent under stirring to precipitate the metal elements on the carrier.

4) a method which is usually called a kneading method, wherein a precipitation agent is added to a solution of the metal elements to form precipitates, then a powder of carrier, hydrogel or hydrosol is added thereto, and the mixture is kneaded.

However, the catalyst may be supported on a carrier by any other method. A solution of the metal elements may be prepared by dissolving soluble salts or complexes of the metal elements in a solvent. For example, as a soluble salt or complex of Ni, nickel nitrate, nickel sulfate, nickel chloride, nickel bromide, nickel iodide, nickel acetate, nickel formate, nickel oxalate, a nickel alkoxide, nickel acetylacetonate or nickel carbonyl may be employed. As a soluble salt or complex of M, scandium acetate, scandium nitrate, scandium chloride, yttrium nitrate, yttrium sulfate, yttrium chloride, yttrium fluoride, yttrium iodide, an yttrium alkoxide, lanthanum nitrate, lanthanum chloride, cerium nitrate, cerium sulfate, praseodymium sulfate, praseodymium nitrate, praseodymium sulfate, neodymium acetate, neodymium chloride, neodymium nitrate, samarium nitrate, samarium sulfate, samarium chloride, samarium fluoride, a samarium alkoxide, europium oxalate, europium chloride, gadolinium acetate, gadolinium chloride, gadolinium nitrate, terbium chloride, terbium acetate, terbium nitrate, dysprosium acetate, dysprosium chloride, dysprosium nitrate, dysprosium sulfate, holmium acetate, holmium nitrate, erbium chloride, erbium acetate, erbium nitrate, erbium oxalate, thulium acetate, thulium nitrate, ytterbium nitrate, ytterbium sulfate, ytterbium chloride, ytterbium iodide, an ytterbium alkoxide, lutetium nitrate, lutetium acetate, lutetium chloride or lutetium sulfate, may be employed. As a soluble salt or complex of Re, rhenium chloride, rhenium bromide, rhenium oxide, rhenium sulfide, ammonium perrhenate or rhenium carbonyl, may, for example, be used. As a soluble salt or complex of Ir, iridium chloride, iridium bromide or iridium sulfide may, for example, be used. As a soluble salt or complex of Pt, platinum chloride, platinum bromide, platinum iodide, platinum oxide, platinum sulfide or tetraammineplatinum(II) chloride, may, for example, be used. Likewise, as a soluble salt or complex of Pd, palladium chloride, palladium nitrate, palladium sulfate or palladium acetate may, for example, be used. After supported on a carrier, the respective catalyst components may be converted to their oxides by hydrolysis and/or calcination, and they may further be converted to metals by reduction. It is difficult to define the conditions for the calcination and reduction, since they vary to large extents depending upon the types of the catalyst components, the types of the carrier and the supporting method However, if an example is given with respect to a case wherein an activated alumina carrier is used, the calcination temperature is preferably from 200° to 700° C. when nitrates are used as starting materials for Ni and M and ammonium perrhenate is used as a starting material for Re. If the temperature is less than 200° C., the decomposition rates of nitrates of Ni and M tend to be low. On the other hand, if the calcination is conducted at a temperature exceeding 700° C., Ni, M and Re tend to be sintered, whereby the catalytic activity tends to be low, and Ni tends to form nickel aluminate, whereby the reducibility tends to deteriorate. As the atmospheric gas for calcination, air or nitrogen may be employed. In a case where reduction is conducted by hydrogen gas, the temperature for reduction is preferably from 300° to 650° C. If the temperature is less than 300° C., the reduction rate of Ni tends to be low. On the other hand, if the temperature exceeds 650° C., Ni, M and Re tend to be sintered, whereby the catalytic activity tends to deteriorate. However, when a carrier having a weaker interaction with Ni, M and Re than activated alumina, such as silica, α-alumina, diatomaceous earth or glass is employed, Ni may sometimes adequately be reduced to nickel metal even at a low temperature at a level of not higher than 200° C. The same conditions for calcination and reduction will apply to the case where X is Ir, Pt or Pd.

In the process of the present invention, M elements to be added to Ni may be used alone or in combination as a mixture of two or more elements With respect to the amount of M to be added to Ni, the atomic ratio of Ni/M is preferably from 0.5 to 100, more preferably from 1 to 80. When a plurality of M elements are used, the total amount of the M elements may be within the above range. If the atomic ratio of Ni/M is less than 0.5 or more than 100, the catalytic activity and selectivity tend to deteriorate. With respect to the ratio of Re, Ir, Pt or Pd to Ni, the atomic ratio of Ni/Re, Ni/Ir, Ni/Pt or Ni/Pd is preferably from 1 to 100, more preferably from 2 to 80. If this atomic ratio is less than 1 or more than 100, the catalytic activity and selectivity tend to deteriorate.

The catalyst to be used in the process of the present invention may be in a powder form or may be molded into a granular, spherical, columnar, cylindrical or pellet form or in a non-specified form. The molding of the catalyst can be conducted by various methods such as a method wherein the catalyst components are supported on a molded carrier, or a method wherein powdery catalyst components, or powdery carrier having the catalyst components supported thereon, is molded by various methods such as tablet molding, extrusion molding, spray drying or rolling granulation. In a case of a suspended bed system, a powdery or granular catalyst may be employed, and in a case of a fixed bed system, a pellet-form, tablet-form, spherical or granular catalyst may be employed When the catalyst is to be molded, a binder such as alumina sol, silica sol, titania sol, acid clay or clay may be incorporated.

In the process of the present invention, the catalyst may be used in an amount sufficient to let the reaction proceed at an industrially useful rate. The amount can not generally be defined, since it varies depending upon whether the reaction system is a suspended bed system or a fixed bed system. In the case of a suspended bed system, it is usual to use the catalyst in an amount of from 0.1 to 20% by weight relative to the total weight of the starting materials. If the amount is less than 0.1% by weight, no adequate reaction rate is obtainable, and if it exceeds 20% by weight, no further significant improvement in the catalytic activity tends to be obtained.

The starting materials to be used in the process of the present invention are an ethanolamine and ammonia and/or an ethylenamine.

In the process of the present invention, the ethanolamine is a compound having an ethylene chain and having a hydroxyl group and an amino group in the molecule, and it may be, for example, monoethanolamine, diethanolamine, triethanolamine, N-(2-aminoethyl)ethanolamine, or N-(2-hydroxyethyl)piperazine. The ethylenamine is a compound having amino groups at both terminals of an ethylene chain, and it may be, for example, ethylenediamine, diethylenetriamine, triethylenetetramine, tetraethylenepentamine, pentaethylenehexamine, piperazine, N-(2-aminoethyl)piperazine or triethylenediamine. Ammonia may be used in a state free from water or in a form of aqueous ammonia.

The combinations of the starting materials to be used in the process of the present invention include:
(1) ammonia and an ethanolamine,
(2) an ethylenamine and an ethanolamine, and
(3) ammonia, an ethylenamine and an ethanolamine.

The reactions in the process of the present invention are consective reactions, whereby a resulting amine serves as a starting material for the subsequent reaction. When monoethanolamine is used as the ethanolamine and ethylenediamine which is the lowest ethylenamine, is used as the starting material, ethylenediamine will be formed in the case of the combination (1) of the starting materials. The resulting ethylenediamine will further react to form diethylenetriamine, triethylenetetramine, piperazine and N-(2-aminoethyl)piperazine. In the combination (2) diethylenetriamine, triethylenetetramine, tetraethylenepentamine, piperazine and N-(2-aminoethyl)piperazine will be formed. Likewise, in the combination (3), ethylenediamine, diethylenetriamine, triethylenetetramine, piperazine and N-(2-aminoethyl)piperazine will be formed Namely, an ethylenamine having the number of ethylene chains increased over the ammonia and/or the ethylenamine used as starting material, will be formed. Further, ethanolamines having the number of ethylene chains increased will also be formed as by-products, but these ethanolamines will also be consumed by the consective reactions.

With respect to the ratio of the starting materials to be used in the process of the present invention, the molar ratio of the ethylenamine/the ethanolamine is preferably from 0.1 to 20, more preferably from 0.5 to 10, and the molar ratio of the ammonia/the ethanolamine is preferably from 1 to 50, more preferably from 5 to 30. If the ethanolamine is too small as compared with the ammonia and the ethylenamine, the reaction pressure will be too high to be practical. On the other hand, if the ethanolamine is too large as compared with the ammonia and the ethylenamine, cyclic amines which are industrially undesirable, such as piperazine, and ethanolamines other than the ethylenamine will be formed substantially as by-products.

In the process of the present invention, the reaction is conducted in the presence of hydrogen. The hydrogen is supplied in a molar ratio of the hydrogen/the ethanolamine of from 0.01 to 5, preferably from 0.02 to 4. If the molar ratio is smaller or larger than the above range, the reaction rate tends to be low.

In the process of the present invention, the reaction is conducted usually at a temperature of from 110° to 290° C., preferably from 140° to 260° C. If the temperature is lower than 110° C., the reaction rate tends to be substantially low, and if it exceeds 290° C., the pressure tends to be high and the decomposition of the amine occurs, such being not practical.

In the process of the present invention, the reaction may be conducted in a liquid phase or in a gas phase. However, in order to produce an ethylenamine of high quality, it is better to conduct the reaction in a liquid phase.

In the process of the present invention, the pressure can not generally be defined, since it varies substantially depending upon the starting materials, the reaction temperature, etc. However, the pressure may be at a level whereby the ethanolamine and the ethylenamine can be maintained in a liquid phase.

In the process of the present invention, a solvent may be employed. As such a solvent, the one capable of dissolving the ethylenamine and ammonia is preferred. For example, water, dioxane, diethylene glycol dimethyl ether or triethylene glycol dimethyl ether may be mentioned. However, other solvents may be employed.

In the process of the present invention, there is no particular restriction as to the reaction method. The reaction may be conducted by a batch method, a semibatch method or a continuous method by a fixed bed system, a fluidized bed system or a mobile bed system.

In the process of the present invention, it is usual that after separating the catalyst from the reaction solution, unreacted starting materials are separated and recovered by distillation. The formed ethylenamines are also separated into the respective components by distillation. The distillation may be conducted in a batch system or in a continuous system.

In the process of the present invention, the starting materials and the formed ethylenamines may be recycled to the reaction zone, as the case requires. By recycling the formed ethylenamines to the reaction zone, it is possible to change the composition of ethylenamine products.

The present invention provides a process for producing an ethylenamine from an ethanolamine, wherein a catalyst comprising Ni, X and M elements having high catalytic activity and high selectivity, is used and thus is very useful from the industrial viewpoint.

Now, the present invention will be described in detail with reference to Examples. However, it should be understood that the present invention is by no means restricted to such specific Examples.

For the sake of convenience, ethylenamines and ethanolamines will be represented by the following abbreviations.

EDA: ethylenediamine
DETA: diethylenetriamine
TETA: triethylenetetramine
TEPA: tetraethylenepentamine PIP: piperazine
AEP: N-(2-aminoethyl)piperazine
MEA: monoethanolamine
AEEA N-(2-aminoethyl)ethanolamine Further, the selectivity will be represented by the following formula.

$$\text{Selectivity (\%)} = \frac{\text{mols of the product} \times \text{number of ethylene chains in the product}}{\text{mols of consumed MEA}} \times 100$$

EXAMPLE 1

4.96 g of nickel(II) nitrate hexahydrate, 0.43 g of yttrium(III) nitrate hexahydrate and 0.14 g of ammonium perrhenate were dissolved in 2.5 g of water, and 7.6 g of an activated alumina molded product (spherical, manufactured by Sumitomo Chemical Co., Ltd.) was immersed therein for one hour. The product was evaporated to dryness by an evaporating dish on a hot water bath and then dried overnight at 120° C. Then, it was calcined at 400° C. for one hour under a dry air stream of 200 ml/min. After calcination, it was again immersed in a solution having 4.96 g of nickel(II) nitrate hexahydrate, 0.43 g of yttrium(III) nitrate hexahydrate and 0.14 g of ammonium perrhenate dissolved in 2.5 g of water. Then, the product was evaporated to dryness by an evaporating dish on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Catalyst 1. The amount of Ni supported on this Catalyst 1 was 20% by weight, the atomic ratio of Ni/Y was 15.2, and the atomic ratio of Ni/Re was 31.7. The X-ray diffraction of the catalyst was measured, whereby only the diffraction peak of nickel was ascertained, and the crystal size of nickel was 7.9 nm as obtained from the Scherrer's formula.

Into a 200 ml stainless steel autoclave equipped with an electromagnetic stirrer, 30 g of MEA and 3 g of Catalyst 1 were charged and flushed with hydrogen. Then, 54 g of ammonia was added, and hydrogen was introduced so that the hydrogen partial pressure became 20 kg/cm² at room temperature. Then, the rotational speed of the stirrer was adjusted to 500 rpm, and the temperature was raised to 200° C., and the temperature was maintained at this level for 3 hours. After completion of the reaction, the reaction solution was analyzed by gas chromatography. As a result, the conversion of MEA was 64.6%, and with respect to the selectivity, EDA was 54.5%, PIP was 11.8%, DETA was 13.0%, AEEA was 8.7%, AEP was 1.3%, TETA was 2.1%, and TEPA was 1.0%. Further, the ratio of EDA/(PIP+AEEA) was 2.66, which represents the ratio of a desired product such as EDA to undesired products such as cyclic products represented by PIP and hydroxyl group-containing amines represented by AEEA.

COMPARATIVE EXAMPLE 1

Comparative Catalyst 1 was prepared in the same manner as for Catalyst 1 except that yttrium(III) nitrate hexahydrate and ammonium perrhenate were not used. The preparation method will be specifically described.

4.96 g of nickel(II) nitrate hexahydrate was dissolved in 2.5 g of water, and 8.0 g of an activated alumina molded product (spherical, manufactured by Sumitomo Chemical Co., Ltd.) was immersed therein for one hour. The product was evaporated to dryness by an evaporating dish on a hot water bath and then dried overnight at 120° C. Then, it was calcined at 400° C. for one hour under a dry air stream of 200 ml/min. After calcination, it was immersed again in a solution having 4.96 g of nickel(II) nitrate hexahydrate dissolved in 2.5 g of water. Then, the product was evaporated to dryness by an evaporating dish on a hot water bath and then dried overnight at 120° C. After drying, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Comparative Catalyst 1. The amount of Ni supported on this Comparative Catalyst 1 was 20% by weight. The X-ray diffraction of this catalyst was measured, whereby only the diffraction peak of nickel was ascertained, and the crystal size of nickel was 9.9 nm as obtained from the Scherrer's formula.

The reaction was conducted in the same manner as in Example 1 except that Comparative Catalyst 1 was used instead of Catalyst 1. As a result, the conversion of MEA was 39.9%, and with respect to the selectivity, EDA was 57.7%, PIP was 5.7%, DETA was 8.4%, AEEA was 18.8%, AEP was 0.3%, TETA was 1.0%, and TEPA was 0.3%. Further, the ratio of EDA/(PIP+AEEA) was 2.38.

COMPARATIVE EXAMPLE 2

Comparative Catalyst 2 was prepared in the same manner as for Catalyst 1 except that ammonium perrhenate was not used. The preparation method will be specifically described.

4.96 g of nickel(II) nitrate hexahydrate and 0.43 g of yttrium(III) nitrate hexahydrate were dissolved in 2.5 g of water, and 7.8 g of an activated alumina molded product (spherical, manufactured by Sumitomo Chemical Co., Ltd.) was immersed therein for one hour Then, the product was evaporated to dryness by an evaporating dish on a hot water bath and then dried overnight at 120° C. After drying, it was calcined at 400° C. for one hour under a dry air stream of 200 ml/min. After calcination, it was again immersed in a solution having 4.96 g nickel(II) nitrate hexahydrate and 0.43 g of yttrium-(III) nitrate hexahydrate dissolved in 2.5 g of water. Then, it was evaporated to dryness by an evaporating dish on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Comparative Catalyst 2. The amount of Ni supported on this comparative catalyst was 20% by weight, and the atomic ratio of Ni/Y was 15.2. The X-ray diffraction of the catalyst was measured, whereby only the diffraction peak of nickel was ascertained, and the crystal size of nickel was 9.2 nm as obtained from the Scherrer's formula.

The reaction was conducted in the same manner as in Example 1 except that Comparative Catalyst 2 was used instead of Catalyst 1. As a result, the conversion of MEA was 55.9%, and with respect to the selectivity, EDA was 54.0%, PIP was 11.4%, DETA was 13.1%, AEEA was 10.3%, AEP was 1.0%, TETA was 1.7%, and TEPA was 0.9%. Further, the ratio of EDA/(PIP+AEEA) was 2.50.

COMPARATIVE EXAMPLE 3

Comparative Catalyst 3 was prepared in the same manner as for Comparative Catalyst 2 except that 0.14 g of ammonium perrhenate was used instead of yttrium-(III) nitrate hexahydrate. The amount of Ni supported on this Comparative Catalyst 3 was 20% by weight, and the atomic ratio of Ni/Re was 31.7. The X-ray diffraction of the catalyst was measured, whereby only the diffraction peak of nickel was ascertained, and the crystal size of nickel was 9.1 nm as obtained from the Scherrer's formula.

The reaction was conducted in the same manner as in Example 1 except that Comparative Catalyst 3 was used instead of Catalyst 1. As a result, the conversion of MEA was 57.9%, and with respect to the selectivity, EDA was 53.6%, PIP was 12.4%, DETA was 10.2%, AEEA was 11.8%, AEP was 1.1%, TETA was 1.6%, and TEPA was 1.0%. Further, the ratio of EDA/(PIP+AEEA) was 2.22.

COMPARATIVE EXAMPLE 4

Comparative Catalyst 4 was prepared in the same manner as for Comparative Catalyst 2 except that 0.15 g of samarium(III) nitrate hexahydrate was used instead of yttrium(III) nitrate hexahydrate, and 7.9 g of the carrier was used. The amount of Ni supported on this Comparative Catalyst 4 was 20% by weight, and the atomic ratio of Ni/Sm was 51.3. The X-ray diffraction of the catalyst was measured, whereby only the diffraction peak of nickel was ascertained, and the crystal size of nickel was 9.5 nm as obtained from the Scherrer's formula.

The reaction was conducted in the same manner as in Example 1 except that Comparative Catalyst 4 was used instead of Catalyst 1. As a result, the conversion of MEA was 50.2%, and with respect to the selectivity, EDA was 55.2%, PIP was 8.7%, DETA was 12.1%, AEEA was 13.8%, AEP was 0.8%, TETA was 1.4%, and TEPA was 0.4%. Further, the ratio of EDA/(PIP+AEEA) was 2.45.

EXAMPLE 2

A catalyst was prepared in the same manner as for Catalyst 1 except that 0.22 g of yttrium(III) nitrate hexahydrate and 7.7 g of the carrier were used. The obtained catalyst was designated as Catalyst 2. The amount of Ni supported on this Catalyst 2 was 20% by weight, the atomic ratio of Ni/Y was 30.3, and the atomic ratio of Ni/Re was 31.7. The X-ray diffraction of the catalyst was measured, whereby only the diffraction peak of nickel was ascertained, and the crystal size of nickel was 8.8 nm as obtained from the Scherrer's formula.

The reaction was conducted in the same manner as in Example 1 except that Catalyst 2 was used instead of Catalyst 1. As a result, the conversion of MEA was 60.8%, and with respect to the selectivity, EDA was 54.2%, PIP was 11.5%, DETA was 12.6%, AEEA was 10.4%, AEP was 1.0%, TETA was 1.7%, and TEPA was 0.9%. Further, the ratio of EDA/(PIP+AEEA) was 2.52.

EXAMPLE 3

Into a 200 ml stainless steel autoclave equipped with an electromagnetic stirrer, 30 g of MEA and 3 g of Catalyst 1 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 500 rpm, and the temperature was raised to 180° C. The temperature was maintained at this level for 7 hours. After completion of the reaction, the reaction solution was analyzed by gas chromatography. As a result, the conversion of MEA was 36.4%, and with respect to the selectivity, EDA was 63.2%, PIP was 5.8%, DETA was 13.3%, AEEA was 9.3%, and TETA was 0.8%. Further, the ratio of EDA/(PIP+AEEA) was 4.18.

EXAMPLE 4

4.96 g of nickel(II) nitrate hexahydrate, 0.22 g of yttrium(III) nitrate hexahydrate, 0.12 g of ytterbium-(III) nitrate tetrahydrate and 0.22 g of ammonium perrhenate were dissolved in 2.5 g of water, and 7.5 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed in a solution having 4.96 g of nickel(II) nitrate hexahydrate, 0.22 g of yttrium(III) nitrate hexahydrate, 0.12 g of ytterbium(III) nitrate tetrahydrate and 0.22 g of ammonium perrhenate dissolved in 2.5 g of water. Then, it was evaporated to dryness, dried, calcined and reduced in the same manner as in Example 1 to obtain Catalyst 3. The amount of Ni supported on this Catalyst 3 was 20% by weight, the atomic ratio of Ni/(Y+Yb) was 20.1, and the atomic ratio of Ni/Re was 21.2. The X-ray diffraction of the catalyst was measured, whereby only the diffraction peak of nickel was ascertained, and the crystal size of nickel was 8.3 nm as obtained from the Scherrer's formula.

The reaction was conducted in the same manner as in Example 1 except that Catalyst 3 was used instead of Catalyst 1. As a result, the conversion of MEA was 63.9%, and with respect to the selectivity, EDA was 54.7%, PIP was 11.9%, DETA was 12.8%, AEEA was 8.9%, AEP was 1.4%, TETA was 2.0%, and TEPA was 1.1%. Further, the ratio of EDA/(PIP+AEEA) was 2.63.

EXAMPLE 5

4.96 g of nickel(II) nitrate hexahydrate, 0.11 g of yttrium(III) nitrate hexahydrate, 0.12 g of ytterbium-(III) nitrate tetrahydrate, 0.074 g of samarium(III) nitrate hexahydrate and 0.072 g of ammonium perrhenate were dissolved in 2.5 g of water, and 7.7 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour in a dry air stream of 200 ml/min. After calcination, it was again immersed in a solution having 4.96 g of nickel(II) nitrate hexahydrate, 0.11 g of yttrium(III) nitrate hexahydrate, 0.12 g of ytterbium(III) nitrate tetrahydrate, 0.074 g of samarium(III) nitrate hexahydrate and 0.072 g of ammonium perrhenate dissolved in 2.5 g of water. Then, it was evaporated to dryness, dried, calcined and reduced in the same manner as in Example 1 to obtain Catalyst 4. The amount of Ni supported on this Catalyst 4 was 20% by weight, the atomic ratio of Ni/(Y+Yb+Sm) was 23.2, and the atomic ratio of Ni/Re was 63.5. The X-ray diffraction of the catalyst was measured, whereby only the diffraction peak of nickel was ascertained, and the crystal size of nickel was 8.7 nm as obtained from the Scherrer's formula.

The reaction was conducted in the same manner as in Example 1 except that Catalyst 4 was used instead of Catalyst 1. As a result, the conversion of MEA was 64.1%, and with respect to the selectivity, EDA was 54.1%, PIP was 13.1%, DETA was 12.5%, AEEA was 8.2%, AEP was 1.5%, TETA was 1.9%, and TEPA was 1.0%. Further, the ratio of EDA/(PIP+AEEA) was 2.54.

EXAMPLES 6 to 18

A catalyst having Ni supported in an amount of 20% by weight was prepared in the same manner as for Catalyst 1 except that the M element and the carrier as identified in Table 1 were used instead of the yttrium(III) nitrate hexahydrate.

The reaction was conducted in the same manner as in Example 1 except that the catalyst as identified in Table 1 was used instead of Catalyst 1. The results of the reaction and the atomic ratio of the M element to Ni of the catalyst are shown in Table 2.

and 1 g of Catalyst 1 were charged and flushed with hydrogen. Then, hydrogen was introduced so that the hydrogen partial pressure became 20 kg/cm$^2$ at room temperature. Then, the rotational speed of the stirrer was adjusted to 500 rpm, and the temperature was raised to 200° C. Then, the temperature was maintained at this level for 3 hours. After completion of the reaction, the reaction solution was analyzed by gas chromatography. As a result, the conversion of MEA was 26.4%, and the composition of the product except for the starting materials and formed water were 19.4% by weight of PIP, 61.7% by weight of DETA, 7.5% by weight of AEEA, 3.0% by weight of AEP and 7.9% by weight of TETA.

EXAMPLE 20

44.9 g of nickel(II) sulfate hexahydrate and 1.40 g of ytterbium(III) nitrate tetrahydrate were dissolved in 200 g of water, and 6 g of diatomaceous earth (manufactured by Johns-Manville Co.) was added thereto. The mixture was maintained at 70° C. under stirring. A solution having 40 g of soda ash dissolved in 150 g of water under heating, was dropwise added thereto over a period of 30 minutes. And then aged for one hour. After the aging, the mixture was cooled to room temperature, and the precipitate was collected by filtration and washed with water. This precipitate was added to a solution having 0.81 g of ammonium perrhenate dissolved in 30 g of water, to obtain a uniform slurry. Then, the slurry was evaporated to dryness on a hot water bath and then dried overnight at 120° C. After drying, it was calcined at 400° C. for one hour under a dry air stream of 200 ml/min. Then, it was reduced at

TABLE 1

| Example No. | Catalyst No. | M element | Reagent | Amount added (g) | Amount of carrier (g) |
|---|---|---|---|---|---|
| Example 6 | Catalyst 5 | Sc | Scandium(III) acetate | 0.49 | 7.6 |
| Example 7 | Catalyst 6 | Pr | Praseodymium(III) nitrate hexahydrate | 0.46 | 7.5 |
| Example 8 | Catalyst 7 | Nd | Neodymium(III) nitrate hexahydrate | 0.30 | 7.6 |
| Example 9 | Catalyst 8 | Sm | Samarium(III) nitrate hexahydrate | 0.15 | 7.7 |
| Example 10 | Catalyst 9 | Eu | Europium(III) chloride hexahydrate | 0.24 | 7.6 |
| Example 11 | Catalyst 10 | Gd | Gadolinium(III) nitrate hexahydrate | 0.14 | 7.7 |
| Example 12 | Catalyst 11 | Tb | Terbium(III) chloride hexahydrate | 0.12 | 7.7 |
| Example 13 | Catalyst 12 | Dy | Dysprosium(III) nitrate hexahydrate | 0.14 | 7.7 |
| Example 14 | Catalyst 13 | Ho | Holmium(III) acetate tetrahydrate | 0.38 | 7.5 |
| Example 15 | Catalyst 14 | Er | Erbium(III) acetate tetrahydrate | 0.25 | 7.6 |
| Example 16 | Catalyst 15 | Tm | Thulium(III) nitrate pentahydrate | 0.26 | 7.6 |
| Example 17 | Catalyst 16 | Yb | Ytterbium(III) nitrate tetrahydrate | 0.37 | 7.5 |
| Example 18 | Catalyst 17 | Lu | Lutetium(III) nitrate dihydrate | 0.23 | 7.6 |

TABLE 2

| Example No. | Catalyst No. | Atomic ratio of Ni/M | Conversion of MEA (%) | EDA (PIP + AEEA) |
|---|---|---|---|---|
| Example 6 | Catalyst 5 | 7.6 | 62.0 | 2.53 |
| Example 7 | Catalyst 6 | 16.0 | 59.9 | 2.56 |
| Example 8 | Catalyst 7 | 24.5 | 60.2 | 2.59 |
| Example 9 | Catalyst 8 | 51.3 | 62.3 | 2.63 |
| Example 10 | Catalyst 9 | 25.8 | 59.9 | 2.58 |
| Example 11 | Catalyst 10 | 53.5 | 63.8 | 2.55 |
| Example 12 | Catalyst 11 | 54.0 | 58.8 | 2.57 |
| Example 13 | Catalyst 12 | 55.3 | 60.4 | 2.58 |
| Example 14 | Catalyst 13 | 18.7 | 59.8 | 2.53 |
| Example 15 | Catalyst 14 | 28.4 | 58.9 | 2.59 |
| Example 16 | Catalyst 15 | 28.7 | 60.3 | 2.55 |
| Example 17 | Catalyst 16 | 19.6 | 64.2 | 2.61 |
| Example 18 | Catalyst 17 | 29.7 | 59.4 | 2.54 |

EXAMPLE 19

Into a 200 ml stainless steel autoclave equipped with an electromagnetic stirrer, 60 g of EDA, 30 g of MEA 400° C. for 2 hours under a gas stream of 90 ml/min of hydrogen and 90 ml/min of nitrogen. At the time of calcination and reduction, the temperature raising rate was adjusted to be 10° C./min. The obtained catalyst was designated as Catalyst 18. The amount of Ni supported on this Catalyst 18 was 58.5% by weight, the atomic ratio of Ni/Yb was 53.1, and the atomic ratio of Ni/Re was 57.2. The X-ray diffraction of the catalyst was measured, whereby only the diffraction peak of nickel was ascertained, and the crystal size of nickel was 6.3 nm as obtained from the Scherrer's formula.

Into a 200 ml stainless steel autoclave equipped with an electromagnetic stirrer, 30 g of MEA and 0.6 g of Catalyst 18 were charged and flushed with hydrogen. Then, 54 g of ammonia was added thereto, and hydrogen was introduced so that the hydrogen partial pressure became 20 kg/cm2 at room temperature. Then, the rotational speed of the stirrer was adjusted to 1000 rpm, and the temperature was raised to 200° C. The temperature was maintained at this level for 3 hours. After completion of the reaction, the reaction solution was analyzed by gas chromatography. As a result, the conversion of MEA was 40.2%, and with respect to the selectivity, EDA was 63.9%, PIP was 6.4%, DETA was 9.9, AEEA was 9.3%, AEP was 0.4%, and TETA was 1.2%. Further, the ratio of EDA/(PIP+AEEA) was 4.08.

EXAMPLE 21

4.96 g of nickel(II) nitrate hexahydrate, 0.43 g of yttrium(III) nitrate hexahydrate and 0.17 g of iridium tetrachloride were dissolved in a mixed solution of 2.5 g of water and 0.5 g of 61% nitric acid, and 7.6 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. Then, it was calcined at 400° C. for one hour under a dry air stream of 200 ml/min. After calcination, it was again immersed for one hour in a solution having 4.96 g of nickel(II) nitrate hexahydrate, 0.43 g of yttrium(III) nitrate hexahydrate and 0.17 g of iridium tetrachloride dissolved in a mixed solution of 2.5 g of water and 0.5 g of 61% nitric acid. Then, the product was evaporated to dryness by an evaporating dish on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to 10° C./min. The obtained catalyst is designates as Catalyst 19. The amount of Ni supported on this Catalyst 19 was 20% by weight, the atomic ratio of Ni/Y was 15.2, and the atomic ratio of Ni/Ir was 33.5. The X-ray diffraction of the catalyst was measured, whereby only the diffraction peak of nickel was ascertained, and the crystal size of nickel was 11.8 nm as obtained from the Scherrer's formula.

Into a 200 ml stainless steel autoclave equipped with an electromagnetic stirrer, 30 g of MEA and 3 g of Catalyst 19 were charged and flushed with hydrogen. Then, 54 g of ammonia was added thereto, and hydrogen was introduced so that the hydrogen partial pressure became 20 kg/cm² al room temperature. Then, the rotational speed of the stirrer was adjusted to 500 rpm, and the temperature was raised to 200° C. The temperature was maintained at this level for 3 hours. After completion of the reaction, the reaction solution was analyzed by gas chromatography. As a result, the conversion of MEA was 63.2%, and with respect to the selectivity, EDA was 53.2%, PIP was 12.5%, DETA was 10.9, AEEA was 6.8%, AEP was 1.5%, TETA was 2.5%, and TEPA was 1.1%. Further, the ratio of EDA/(PIP+AEEA) was 2.76.

COMPARATIVE EXAMPLE 5

Comparative Catalyst 5 was prepared in the same manner as for Catalyst 19 except that yttrium(III) nitrate hexahydrate was not used. The preparation method will be specifically described. 4.96 g of nickel-(II) nitrate hexahydrate and 0.17 g of iridium tetrachloride were dissolved in a mixed solution of 2.5 g of water and 0.5 g of 61% nitric acid, and 7.7 g of an activated alumina molded product (spherical, manufactured by Sumitomo Chemical Co., Ltd.) was immersed therein for one hour. The product was evaporated to dryness by an evaporating dish on a hot water bath and dried overnight at 120° C. Then, it was calcined at 400° C. for one hour under a dry air stream of 200 ml/min. After calcination, it was again immersed in a solution having 4.96 g of nickel(II) nitrate hexahydrate and 0.17 g of iridium tetrachloride dissolved in a mixed solution of 2.5 g of water and 0.5 g of 61% nitric acid. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designates as Comparative Catalyst 5. The amount of Ni supported on this Comparative Catalyst 5 was 20% by weight, and the atomic ratio of Ni/Ir was 33.5. The X-ray diffraction of the Comparative Catalyst 5 was measured, whereby only the diffraction peak of nickel was ascertained, and the crystal size of nickel was 11.2 nm as obtained from the Scherrer's formula.

The reaction was conducted in the same manner as in Example 21 except that Comparative Catalyst 5 was used instead of Catalyst 19. As a result, the conversion of MEA was 58.6%, and with respect to the selectivity, EDA was 54.9%, PIP was 11.2%, DETA was 10.4%, AEEA was 9.9%, AEP was 1.3%, TETA was 1.4%, and TEPA was 0.6%. Further, the ratio of EDA/(PIP-+AEEA) was 2.60.

EXAMPLE 22

A catalyst was prepared in the same manner as for Catalyst 19 except that 0.085 g of iridium tetrachloride and 7.7 g of the carrier were used. The obtained catalyst was designated as Catalyst 20. The amount of Ni supported on this Catalyst 20 was 20% by weight, the atomic ratio of Ni/Y was 15.2, and the atomic ratio of Ni/Ir was 67.0. The X-ray diffraction of Catalyst 20 was measured, whereby only the diffraction peak of nickel was ascertained, and the crystal size of nickel was 9.1 nm as obtained from the Scherrer's formula.

The reaction was conducted in the same manner as in Example 21 except that Catalyst 20 was used instead of Catalyst 19. As a result, the conversion of MEA was 66.2%, and with respect to the selectivity, EDA was 50.4%, PIP was 12.6%, DETA was 10.8%, AEEA was 6.5%, AEP was 1.5%, TETA was 2.7%, and TEPA was 1.1%. Further, the ratio of EDA/(PIP+AEEA) was 2.64.

EXAMPLE 23

Into a 200 ml stainless steel autoclave equipped with an electromagnetic stirrer, 30 g of MEA and 3 g of Catalyst 19 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 500 rpm, and the temperature was raised to 180° C. The temperature was maintained at this level for 7 hours. After completion of the reaction, the reaction solution was analyzed by gas chromatography. As a result, the conversion of MEA was 38.2%, and with respect to the selectivity, EDA was 62.7%, PIP was 5.6%, DETA was 14.3%, AEEA was 8.7%, and TETA was 0.9%. Further, the ratio of EDA/(PIP+AEEA) was 4.38.

EXAMPLE 24

4.96 g of nickel(II) nitrate hexahydrate, 0.22 g of yttrium(III) nitrate hexahydrate, 0.12 g of ytterbium(III) nitrate tetrahydrate and 0.17 g of iridium tetrachloride were dissolved in 2.5 g of water and 0.5 g of 61% nitric acid, and 7.5 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed for one hour in a solution having 4.96 g of nickel(II) nitrate hexahydrate, 0.22 g of yttrium(III) nitrate hexahydrate, 0.12 g of ytterbium(III) nitrate tetrahydrate and 0.17 g of iridium tetrachloride dissolved in 2.5 g of water and 0.5 g of 61% nitric acid. Then, it was evaporated to dryness, dried, calcined and reduced in the same manner as in Example 21 to obtain Catalyst 21. The amount of Ni supported on this Catalyst 21 was 20% by weight, the atomic ratio of Ni/(Y+Yb) was 20.1, and the atomic ratio of Ni/Ir was 33.5. The X-ray diffraction of Catalyst 21 was measured, whereby only the diffraction peak of nickel was ascertained, and the crystal size of nickel was 10.3 nm as obtained from the Scherrer's formula.

The reaction was conducted in the same manner as in Example 21 except that Catalyst 21 was used instead of Catalyst 19. As a result, the conversion of MEA was 65.2%, and with respect to the selectivity, EDA was 52.2%, PIP was 12.9%, DETA was 10.7%, AEEA was 7.0%, AEP was 1.3%, TETA was 2.2%, and TEPA was 1.3%. Further, the ratio of EDA/(PIP+AEEA) was 2.62.

EXAMPLE 25

4.96 g of nickel(II) nitrate hexahydrate, 0.11 g of yttrium(III) nitrate hexahydrate, 0.12 g of ytterbium(III) nitrate tetrahydrate, 0.074 g of samarium(III) nitrate hexahydrate and 0.085 g of iridium tetrachloride were dissolved in a mixed solution of 2.5 g of water and 0.5 g of 61% nitric acid, and 7.7 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed for one hour in a solution having 4.96 g of nickel(II) nitrate hexahydrate, 0.11 g of yttrium(III) nitrate hexahydrate, 0.12 g of ytterbium(III) nitrate tetrahydrate, 0.074 g of samarium(III) nitrate hexahydrate and 0.085 g of iridium tetrachloride dissolved in a mixed solution of 2.5 g of water and 0.5 g of 61% nitric acid. Then, it was evaporated to dryness, dried, calcined and reduced in the same manner as in Example 21 to obtain Catalyst 22. The amount of Ni supported on this Catalyst 22 was 20% by weight, the atomic ratio of Ni/(Y+Yb+Sm) was 23.2, and the atomic ratio of Ni/Ir was 67.0. The X-ray diffraction of Catalyst 22 was measured, whereby only the diffraction peak of nickel was ascertained, and the crystal size of nickel was 9.6 nm as obtained from the Scherrer's formula.

The reaction was conducted in the same manner as in Example 21 except that Catalyst 22 was used instead of Catalyst 19. As a result, the conversion of MEA was 65.8%, and with respect to the selectivity, EDA was 52.4%, PIP was 12.5%, DETA was 10.4%, AEEA was 6.8%, AEP was 1.5%, TETA was 2.3%, and TEPA was 1.4%. Further, the ratio of EDA/(PIP+AEEA) was 2.72.

EXAMPLES 26 to 38

A catalyst having Ni supported in an amount of 20% by weight, was prepared in the same manner as for Catalyst 19 except that the M element and the carrier as identified Table 3 were used instead of the yttrium(III) nitrate hexahydrate.

The reaction was conducted in the same manner as in Example 21 except that the catalyst as identified in Table 3 was used instead of Catalyst 19. The results of the reaction and the atomic ratio of the M element to Ni of the catalyst are shown in Table 4.

TABLE 3

| Catalyst No. | M element | Reagent | Amount added (g) | Amount of carrier (g) |
|---|---|---|---|---|
| Catalyst 23 | Sc | Scandium(III) acetate | 0.49 | 7.6 |
| Catalyst 24 | Pr | Praseodymium(III) nitrate hexahydrate | 0.15 | 7.7 |
| Catalyst 25 | Nd | Neodymium(III) nitrate hexahydrate | 0.30 | 7.6 |
| Catalyst 26 | Sm | Samarium(III) nitrate hexahydrate | 0.44 | 7.5 |
| Catalyst 27 | Eu | Europium(III) nitrate hexahydrate | 0.29 | 7.6 |
| Catalyst 28 | Gd | Gadolinium(III) nitrate hexahydrate | 0.29 | 7.6 |
| Catalyst 29 | Tb | Terbium(III) chloride hexahydrate | 0.12 | 7.7 |
| Catalyst 30 | Dy | Dysprosium(III) chloride hexahydrate | 0.12 | 7.7 |
| Catalyst 31 | Ho | Holmium(III) nitrate tetrahydrate | 0.32 | 7.5 |
| Catalyst 32 | Er | Erbium(III) acetate tetrahydrate | 0.25 | 7.6 |
| Catalyst 33 | Tm | Thulium(III) chloride hexahydrate | 0.23 | 7.6 |
| Catalyst 34 | Yb | Ytterbium(III) nitrate tetrahydrate | 0.37 | 7.5 |
| Catalyst 35 | Lu | Lutetium(III) nitrate dihydrate | 0.23 | 7.6 |

TABLE 4

| Example No. | Catalyst No. | Atomic ratio of Ni/M | Conversion of MEA (%) | EDA (PIP + AEEA) |
|---|---|---|---|---|
| Example 26 | Catalyst 23 | 7.6 | 63.6 | 2.66 |
| Example 27 | Catalyst 24 | 49.5 | 61.2 | 2.71 |
| Example 28 | Catalyst 25 | 24.5 | 61.4 | 2.73 |
| Example 29 | Catalyst 26 | 17.2 | 63.7 | 2.70 |
| Example 30 | Catalyst 27 | 26.2 | 62.4 | 2.69 |
| Example 31 | Catalyst 28 | 26.5 | 61.7 | 2.66 |
| Example 32 | Catalyst 29 | 54.0 | 61.2 | 2.71 |
| Example 33 | Catalyst 30 | 53.6 | 62.1 | 2.68 |
| Example 34 | Catalyst 31 | 18.7 | 61.2 | 2.69 |
| Example 35 | Catalyst 32 | 28.4 | 62.1 | 2.69 |
| Example 36 | Catalyst 33 | 28.4 | 61.9 | 2.64 |
| Example 37 | Catalyst 34 | 19.6 | 63.5 | 2.72 |
| Example 38 | Catalyst 35 | 29.7 | 62.6 | 2.68 |

EXAMPLE 39

Into a 200 ml stainless steel autoclave equipped with an electromagnetic stirrer, 60 g of EDA, 30 g of MEA and 1 g of Catalyst 19 were introduced and flushed with hydrogen. Then, hydrogen was introduced so that the hydrogen partial pressure became 20 kg/cm$^2$ at room temperature. Then, the rotational speed of the stirrer was adjusted to 500 rpm, and the temperature was raised to 200° C. The temperature was maintained at this level for 3 hours. After completion of the reaction, the reaction solution was analyzed by gas chromatography. As a result, the conversion of MEA was 27.8%, and the composition of the product except for the starting materials and formed water was 19.3% by weight of PIP, 62.6% by weight of DETA, 6.4% by weight of AEEA, 3.2% by weight of AEP and 7.6% by weight of TETA.

EXAMPLE 40

44.9 g of nickel(II) sulfate hexahydrate and 1.40 g of ytterbium(III) nitrate tetrahydrate were dissolved in 200 g of water, and 6 g of diatomaceous earth (manufactured by Johns-Manville Co.) was added. The mixture was maintained at 70° C. under stirring. To this mixture, a solution having 40 g of soda ash dissolved in 150 g of water under heating, was dropwise added, and the mixture was aged for one hour. After aging, the mixture was cooled to room temperature, and the precipitate was collected by filtration and washed with water. This precipitate was added to a solution having 0.97 g of iridium tetrachloride dissolved in 30 g of water and 61% nitric acid, to obtain a uniform slurry. Then, this slurry was evaporated to dryness on a hot water bath and then dried overnight at 120° C. After drying, it was dried at 400° C. overnight under a dry air stream of 200 ml/min. Then, it was reduced at 400° C. for 2 hours under a ga stream of 90 ml/min of hydrogen and 90 ml/min of nitrogen. At the time of calcination and reduction, the temperature raising rate was adjusted to be 10° C./min. The obtained catalyst was designated as Catalyst 36. The amount of Ni supported on this Catalyst 36 was 58.5% by weight, the atomic ratio of Ni/Yb was 52.6, and the atomic ratio of Ni/Ir was 58.8. The X-ray diffraction of Catalyst 36 was measured, whereby only the diffraction peak of nickel was ascertained, and the crystal size of nickel was 8.9 nm as obtained from the Scherrer's formula.

Into a 200 ml stainless steel autoclave equipped with an electromagnetic stirrer, 30 g of MEA and 0.6 g of Catalyst 36 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 1000 rpm, and the temperature was raised to 200° C. The temperature was maintained at this level for 3 hours. After completion of the reaction, the reaction solution was analyzed by gas chromatography. As a result, the conversion of MEA was 41.4%, and with respect to the selectivity, EDA was 62.5%, PIP was 6.5%, DETA was 9.9%, AEEA was 9.1%, AEP was 0.5%, and TETA was 0.4%. Further, the ratio of EDA/(PIP+AEEA) was 4.01.

EXAMPLE 41

4.96 g of nickel(II) nitrate hexahydrate, 0.43 g of yttrium(III) nitrate hexahydrate and 0.18 g of tetraammineplatinum(II) chloride monohydrate were dissolved in 2.5 g of water, and 7.6 g of an activated alumina molded product (spherical, manufactured by Sumitomo Chemical Co., Ltd.) was immersed therein for one hour. The product was evaporated to dryness by an evaporating dish on a hot water bath and then dried overnight at 120° C. Then, it was calcined at 400° C. for one hour under a dry air stream of 200 ml/min. After calcination, it was again immersed for one hour in a solution having 4.96 g of nickel(II) nitrate hexahydrate, 0.43 g of yttrium(III) nitrate hexahydrate and 0.18 g of tetraammineplatinum(II) chloride monohydrate dissolved in 2.5 g of water. Then, it was evaporated to dryness by an evaporating dish on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Catalyst 37. The amount of Ni supported on this Catalyst 37 was 20% by weight, the atomic ratio of Ni/Y was 15.2, and the atomic ratio of Ni/Pt was 33.4. The X-ray diffraction of Catalyst 37 was measured, whereby only the diffraction peak of nickel was ascertained, and the crystal size of nickel was 9.1 nm as obtained from the Scherrer's formula.

Into a 200 ml stainless steel autoclave equipped with an electromagnetic stirrer, 30 g of MEA and 3 g of Catalyst 37 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 500 rpm, and the temperature was raised to 200° C. The temperature was maintained at this level for 3 hours. After completion of the reaction, the reaction solution was analyzed by gas chromatography. As a result, the conversion of MEA was 59.8%, and with respect to the selectivity, EDA was 51.9%, PIP was 9.4%, DETA was 8.5%, AEEA was 7.8%, AEP was 1.0%, TETA was 1.6%, and TEPA was 0.8%. Further, the ratio of EDA/(PIP+AEEA) was 3.01.

COMPARATIVE EXAMPLE 6

Comparative Catalyst 6 was prepared in the same manner as for Catalyst 37 except that yttrium(III) nitrate hexahydrate was not used. The preparation method will be specifically described.

4.96 g of nickel(II) nitrate hexahydrate, and 0.18 g of tetraammineplatinum(II) chloride monohydrate were dissolved in 2.5 g of water, and 7.8 g of an activated alumina molded product (spherical, manufactured by Sumitomo Chemical Co., Ltd.) was immersed therein for one hour. The product was evaporated to dryness by an evaporating dish on a hot water bath and then dried overnight at 120° C. Then, it was calcined at 400° C. for one hour under a dry air stream of 200 ml/min. After calcination, it was again immersed for one hour in a solution having 4.96 g of nickel(II) nitrate hexahydrate, and 0.18 g of tetraammineplatinum(II) chloride monohydrate dissolved in 2.5 g of water. Then, it was evaporated to dryness by an evaporating dish on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Comparative Catalyst 6. The amount of Ni supported on this Comparative Catalyst 6 was 20% by weight, and the atomic ratio of Ni/Pt was 33.4. The X-ray diffraction of Comparative Catalyst 6 was measured, whereby only the diffraction peak of nickel was ascertained, and the crystal size of nickel was 11.0 nm as obtained from the Scherrer's formula.

The reaction was conducted in the same manner as in Example 41 except that Comparative Catalyst 6 was used instead of Catalyst 37. As a result, the conversion of MEA was 54.7%, and with respect to the selectivity, EDA was 53.3%, PIP was 8.6%, DETA was 8.2%, AEEA was 11.5%, AEP was 0.9%, TETA was 1.5%, and TEPA was 0.8%. Further, the ratio of EDA/(PIP+AEEA) was 2.65.

EXAMPLE 42

A catalyst was prepared in the same manner as in Catalyst 37 except that 0.090 g of tetraammineplatinum(II) chloride monohydrate and 7.7 g of the carrier were used. The obtained catalyst was designated as Catalyst 38. The amount of Ni supported on this Catalyst 38 was 20% by weight, the atomic ratio of Ni/Y was 15.2, and the atomic ratio of Ni/Pt was 66.7. The X-ray diffraction of Catalyst 38 was measured, whereby only the diffraction peak of nickel was ascertained, and the crystal size of nickel was 9.3 nm as obtained from the Scherrer's formula.

The reaction was conducted in the same manner as in Example 41 except that Catalyst 38 was used instead of Catalyst 37. As a result, the conversion of MEA was 61.2%, and with respect to the selectivity, EDA was 51.5%, PIP was 9.1%, DETA was 8.6%, AEEA was 7.5%, AEP was 1.2%, TETA was 1.8%, and TEPA was 1.0%. Further, the ratio of EDA/(PIP+AEEA) was 3.10.

EXAMPLE 43

Into a 200 ml stainless steel autoclave equipped with an electromagnetic stirrer, 30 g of MEA and 3 g of Catalyst 37 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 500 rpm, and the temperature was raised to 180° C. The temperature was maintained at this level for 8 hours. After completion of the reaction, the reaction solution was analyzed by gas chromatography. As a result, the conversion of MEA was 34.8%, and with respect to the selectivity, EDA was 65.3%, PIP was 4.9%, DETA was 12.6%, AEEA was 11.2%, and TETA was 0.7%. Further, the ratio of EDA/(PIP+AEEA) was 4.06.

EXAMPLE 44

4.96 g of nickel(II) nitrate hexahydrate, 0.22 g of yttrium(III) nitrate hexahydrate, 0.12 g of ytterbium(III) nitrate tetrahydrate and 0.18 g of tetraammineplatinum(II) chloride monohydrate were dissolved in 2.5 g of water, and 7.5 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed for one hour in a solution having 4.96 g of nickel(II) nitrate hexahydrate, 0.22 g of yttrium(III) nitrate hexahydrate, 0.12 g of ytterbium(III) nitrate tetrahydrate and 0.18 g of tetraammineplatinum(II) chloride monohydrate dissolved in 2.5 g of water. Then, it was evaporated to dryness, dried, calcined and reduced in the same manner as in Example 41 to obtain Catalyst 39. The amount of Ni supported on this Catalyst 39 was 20% by weight, and the atomic ratio of Ni/(Y+Yb) was 20.1, and the atomic ratio of Ni/Pt was 33.4. The X-ray diffraction of Catalyst 39 was measured, whereby only the diffraction peak of nickel was ascertained, and the crystal size of nickel was 10.1 nm as obtained from the Scherrer's formula.

The reaction was conducted in the same manner as in Example 41 except that Catalyst 39 was used instead of Catalyst 37. As a result, the conversion of MEA was 59.4%, and with respect to the selectivity, EDA was 53.1%, PIP was 9.2%, DETA was 8.8%, AEEA was 8.9%, AEP was 1.0%, TETA was 1.4%, and TEPA was 0.6%. Further, the ratio of EDA/(PIP+AEEA) was 2.93.

EXAMPLE 45

4.96 g of nickel(II) nitrate hexahydrate, 0.11 g of yttrium(III) nitrate hexahydrate, 0.12 g of ytterbium(III) nitrate tetrahydrate, 0.074 g of samarium(III) nitrate hexahydrate and 0.090 g of tetraammineplatinum(II) chloride monohydrate were dissolved in 2.5 g of water, and 7.7 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed for one hour in a solution having 4.96 g of nickel(II) nitrate hexahydrate, 0.11 g of yttrium(III) nitrate hexahydrate, 0.12 g of ytterbium-(III) nitrate tetrahydrate, 0.074 g of samarium(III) nitrate hexahydrate and 0.090 g of tetraammineplatinum-(II) chloride monohydrate dissolved in 2.5 g of water. Then, it was evaporated to dryness, dried, calcined and reduced in the same manner as in Example 41 to obtain Catalyst 40. The amount of Ni supported on this Catalyst 40 was 20% by weight, the atomic ratio of Ni/(Y+Yb+Sm) was 23.2, and the atomic ratio of Ni/Pt was 66.7. The X-ray diffraction of Catalyst 40 was measured, whereby only the diffraction peak of nickel was ascertained, and the crystal size of nickel was 9.6 nm as obtained from the Scherrer's formula.

The reaction was conducted in the same manner as in Example 41 except that Catalyst 40 was used instead of Catalyst 37. As a result, the conversion of MEA was 60.4%, and with respect to the selectivity, EDA was 51.8%, PIP was 8.9%, DETA was 8.5%, AEEA was 7.9%, AEP was 1.2%, TETA was 1.7%, and TEPA was 1.1%. Further, the ratio of EDA/(PIP+AEEA) was 3.08.

EXAMPLES 46 to 58

A catalyst having Ni supported in an amount of 20% by weight, was prepared in the same manner as for Catalyst 37 except that the M element and the carrier as identified Table 5 were used instead of the yttrium(III) nitrate hexahydrate.

The reaction was conducted in the same manner as in Example 41 except that the catalyst as identified in Table 5 was used instead of Catalyst 37. The results of the reaction and the atomic ratio of the M element to Ni of the catalyst are shown in Table 6.

EXAMPLE 59

Into a 200 ml stainless steel autoclave equipped with an electromagnetic stirrer, 60 g of EDA, 30 g of MEA and 1 g of Catalyst 37 were charged and flushed with hydrogen. Then, hydrogen was introduced so that the hydrogen partial pressure became 20 kg/cm$^2$ at room temperature. Then, the rotational speed of the stirrer was adjusted to 500 rpm, and the temperature was raised to 200° C. The temperature was maintained at this level for 3 hours. After completion of the reaction, the reaction solution was analyzed by gas chromatography. As a result, the conversion of MEA was 23.7%, and the composition of products except for starting materials and formed water was 19.1% by weight of PIP, 60.2% by weight of DETA, 8.2% by weight of AEEA, 3.1% by weight of AEP and 6.5% by weight of TETA.

EXAMPLE 60

44.9 g of nickel(II) sulfate hexahydrate and 1.40 g of ytterbium(III) nitrate tetrahydrate were dissolved in 200 g of water, and 6 g of diatomaceous earth (manufactured by Johns-Manville Co.) was added thereto. The mixture was maintained at 70° C. under stirring. To this mixture, a solution having 40 g of soda ash dissolved in 150 g of water under heating, was dropwise added over a period of 30 minutes, and the mixture was aged for one hour. After the aging, the mixture was cooled to room temperature, and the precipitate was collected by filtration and washed with water. This precipitate was added to a solution having 1.01 g of tetraammineplatinum(II) chloride monohydrate dissolved in 30 g of water, to obtain a uniform slurry. Then, this slurry was evaporated to dryness on a hot water bath and then dried overnight at 120° C. After drying, it was dried over-

TABLE 5

| Catalyst No. | M element | Reagent | Amount added (g) | Amount of carrier (g) |
|---|---|---|---|---|
| Catalyst 41 | Sc | Scandium(III) acetate | 0.49 | 7.6 |
| Catalyst 42 | Pr | Praseodymium(III) chloride hexahydrate | 0.38 | 7.5 |
| Catalyst 43 | Nd | Neodymium(III) nitrate hexahydrate | 0.15 | 7.7 |
| Catalyst 44 | Sm | Samarium(III) nitrate hexahydrate | 0.15 | 7.7 |
| Catalyst 45 | Eu | Europium(III) nitrate hexahydrate | 0.29 | 7.6 |
| Catalyst 46 | Gd | Gadolinium(III) nitrate hexahydrate | 0.29 | 7.6 |
| Catalyst 47 | Tb | Terbium(III) nitrate hexahydrate | 0.14 | 7.7 |
| Catalyst 48 | Dy | Dysprosium(III) nitrate hexahydrate | 0.23 | 7.6 |
| Catalyst 49 | Ho | Holmium(III) acetate tetrahydrate | 0.25 | 7.6 |
| Catalyst 50 | Er | Erbium(III) chloride tetrahydrate | 0.11 | 7.7 |
| Catalyst 51 | Tm | Thulium(III) nitrate pentahydrate | 0.40 | 7.5 |
| Catalyst 52 | Yb | Ytterbium(III) nitrate tetrahydrate | 0.37 | 7.5 |
| Catalyst 53 | Lu | Lutetium(III) nitrate dihydrate | 0.23 | 7.6 |

TABLE 6

| Example No. | Catalyst No. | Atomic ratio of Ni/M | Conversion of MEA (%) | EDA (PIP + AEEA) |
|---|---|---|---|---|
| Example 46 | Catalyst 41 | 7.6 | 58.7 | 3.15 |
| Example 47 | Catalyst 42 | 15.9 | 57.8 | 3.09 |
| Example 48 | Catalyst 43 | 49.8 | 60.1 | 2.97 |
| Example 49 | Catalyst 44 | 51.3 | 61.2 | 2.88 |
| Example 50 | Catalyst 45 | 26.2 | 58.9 | 3.01 |
| Example 51 | Catalyst 46 | 26.5 | 59.2 | 3.06 |
| Example 52 | Catalyst 47 | 55.2 | 57.9 | 2.89 |
| Example 53 | Catalyst 48 | 28.0 | 59.2 | 3.03 |
| Example 54 | Catalyst 49 | 28.3 | 58.7 | 2.97 |
| Example 55 | Catalyst 50 | 59.2 | 58.2 | 2.87 |
| Example 56 | Catalyst 51 | 19.0 | 60.1 | 3.07 |
| Example 57 | Catalyst 52 | 19.6 | 60.4 | 3.21 |
| Example 58 | Catalyst 53 | 29.7 | 59.1 | 3.11 | night at 400° C. under a dry air stream of 200 ml/min. Then, it was reduced at 400° C. for 2 hours under a gas stream of 90 ml/min of hydrogen and 90 ml/min of nitrogen. At the time of calcination and reduction, the temperature raising rate was adjusted to be 10° C./min. The obtained catalyst was designated as Catalyst 54. The amount of Ni supported on this Catalyst 54 was 58.5% by weight, the atomic ratio of Ni/Yb was 52.6, and the atomic ratio of Ni/Pt was 59.6. The X-ray diffraction of Catalyst 54 was measured, whereby only the diffraction peak of nickel was ascertained, and the crystal size of nickel was 8.8 nm as obtained from the Scherrer's formula.

Into a 200 ml stainless steel autoclave equipped with an electromagnetic stirrer, 30 g of MEA and 0.6 g of Catalyst 54 were charged and flushed with hydrogen. Then, 54 g of ammonia was added thereto, and hydrogen was introduced so that the hydrogen partial pressure became 20 kg/cm² at room temperature. Then, the rotational speed of the stirrer was adjusted to 1000 rpm, and the temperature was raised to 200° C. The temperature was maintained at this level for 3 hours. After completion of the reaction, the reaction solution was analyzed by gas chromatography. As a result, the conversion of MEA was 39.7%, and with respect to the selectivity, EDA was 64.2%, PIP was 6.3%, DETA was 9.7, AEEA was 10.1%, AEP was 0.3%, and TETA was 6.3%. Further, the ratio of EDA/(PIP+AEEA) was 3.91.

EXAMPLE 61

4.96 g of nickel(II) nitrate hexahydrate, 0.43 g of yttrium(III) nitrate hexahydrate and 0.22 g of palladium(III) nitrate were dissolved in 2.5 g of water, and 7.6 g of an activated alumina molded product (spherical, manufactured by Sumitomo Chemical Co., Ltd.) was immersed therein for one hour. Then, this product was evaporated to dryness by an evaporating dish on a hot water bath and then dried overnight at 120° C. Then, it was calcined at 400° C. for one hour under a dry air stream of 200 ml/min. After calcination, it was again immersed in a solution having 4.96 g of nickel(II) nitrate hexahydrate, 0.43 g of yttrium(III) nitrate hexahydrate and 0.22 g of palladium(III) nitrate dissolved in 2.5 g of water. The product was evaporated to dryness by an evaporating dish on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Catalyst 55. The amount of Ni supported on this Catalyst 55 was 20% by weight, the atomic ration of Ni/Y was 15.2, and the atomic ration of Ni/Pd was 17.9. The X-ray diffraction of Catalyst 55 was measured, whereby only the diffraction peak of nickel was ascertained, and the crystal size of nickel was 9.9 nm as obtained from the Scherrer's formula.

Into a 200 ml stainless steel autoclave equipped with an electromagnetic stirrer, 30 g of MEA and 3 g of Catalyst 55 were charged and flushed with hydrogen. Then, 54 g of ammonia was added thereto, and hydrogen was introduced so that the hydrogen partial pressure became 20 kg/cm² at room temperature. Then, the rotational speed of the stirrer was adjusted to 500 rpm, and the temperature was raised to 200° C. The temperature was maintained at this level for 3 hours. After completion of the reaction, the reaction solution was analyzed by gas chromatography. As a result, the conversion of MEA was 62.3%, and with respect tot he selectivity, EDA was 54.2%, PIP was 11.9%, DETA was 12.9%, AEEA was 8.7%, AEP was 1.4%, TETA was 2.3%, and TEPA was 0.8%. Further, the ratio of EDA/(PIP+AEEA) was 2.63.

COMPARATIVE EXAMPLE 7

Comparative Catalyst 7 was prepared in the same manner as for Comparative Catalyst 1 except that 0.22 g of palladium(III) nitrate was used instead of yttrium-(III) nitrate hexahydrate. The amount of Ni supported on this Comparative Catalyst 7 was 20% by weight, and the atomic ratio of Ni/Pd was 17.9. The X-ray diffraction of the catalyst was measured, whereby only the diffraction peak of nickel was ascertained, and the crystal size of nickel was 9.4 nm as obtained from the Scherrer's formula.

The reaction was conducted in the same manner as in Example 61 except that Comparative Catalyst 7 was used instead of Catalyst 55. As a result, the conversion of MEA was 45.6%, and with respect to the selectivity, EDA was 55.3%, PIP was 6.1%, DETA was 8.8%, AEEA was 16.0%, AEP was 0.8%, TETA was 1.6%, and TEPA was 0.8%. Further, the ratio of EDA/(PIP-+AEEA) was 2.50.

COMPARATIVE EXAMPLE 8

Comparative Catalyst 8 was prepared in the same manner as for Comparative Catalyst 1 except that 0.12 g of ytterbium(III) nitrate tetrahydrate was used instead of yttrium(III) nitrate hexahydrate, and 7.9 g of the carrier was used. The amount of Ni supported on this Comparative Catalyst 8 was 20% by weight, and the atomic ratio of Ni/Yb was 58.8. The X-ray diffraction of the catalyst was measured, whereby only the diffraction peak of nickel was ascertained, and the crystal size of nickel was 9.7 nm as obtained from the Scherrer's formula.

The reaction was conducted in the same manner as in Example 61 except that Comparative Catalyst 8 was used instead of Catalyst 55. As a result, the conversion of MEA was 51.0%, and with respect to the selectivity, EDA was 54.9%, PIP was 8.2%, DETA was 12.3%, AEEA was 14.4%, AEP was 0.7%, TETA was 1.5%, and TEPA was 0.3%. Further, the ratio of EDA/(PIP-+AEEA) was 2.43.

EXAMPLE 62

A catalyst was prepared in the same manner as for Catalyst 55 except that 0.22 g of yttrium(III) nitrate hexahydrate and 7.7 g of the carrier were used. The obtained catalyst was designated as Catalyst 56. The amount of Ni supported on this Catalyst 56 was 20% by weight, the atomic ratio of Ni/Y was 30.3, and the atomic ratio of Ni/Pd was 17.9. The X-ray diffraction of the catalyst was measured, whereby only the diffraction peak of nickel was ascertained, and the crystal size of nickel was 9.2 nm as obtained from the Scherrer's formula.

The reaction was conducted in the same manner as in Example 61 except that Catalyst 56 was used instead of Catalyst 55. As a result, the conversion of MEA was 61.1%, and with respect to the selectivity, EDA was 53.8%, PIP was 12.0%, DETA was 13.0%, AEEA was 9.2%, AEP was 0.9%, TETA was 1.8%, and TEPA was 0.8%. Further, the ratio of EDA/(PIP+AEEA) was 2.54.

EXAMPLE 63

Into a 200 ml stainless steel autoclave equipped with an electromagnetic stirrer, 30 g of MEA and 3 g of Catalyst 55 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 500 rpm, and the temperature was raised to 180° C. The temperature was maintained at this level for 6 hours. After completion of the reaction, the reaction solution was analyzed by gas chromatography. As a result, the conversion of MEA was 34.7%, and with respect to the selectivity, EDA was 62.8%, PIP was 5.6%, DETA was 13.9%, AEEA was 9.9%, and TETA was 0.9%. Further, the ratio of EDA/(PIP+AEEA) was 4.05.

EXAMPLE 64

4.96 g of nickel(II) nitrate hexahydrate, 0.22 g of yttrium(III) nitrate hexahydrate, 0.14 g of gadolinium(III) nitrate hexahydrate and 0.32 g of palladium(II) nitrate were dissolved in 2.5 g of water, and 7.5 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed in a solution having 4.96 g of nickel(II) nitrate hexahydrate, 0.22 g of yttrium(III) nitrate hexahydrate, 0.14 g of gadolinium(III) nitrate hexahydrate and 0.32 g of palladium(III) nitrate dissolved in 2.5 g of water. Then, the product was evaporated to dryness, dried, calcined and reduced in the same manner as in Example 61 to obtain Catalyst 57. The amount of Ni supported on this Catalyst 57 was 20% by weight, the atomic ratio of Ni/(Y+Gd) was 19.4, and the atomic ratio of Ni/Pd was 12.1. The X-ray diffraction of the catalyst was measured, whereby only the diffraction peak of nickel was ascertained, and the crystal size of nickel was 8.9 nm as obtained from the Scherrer's formula.

The reaction was conducted in the same manner as in Example 61 except that Catalyst 57 was used instead of Catalyst 55. As a result, the conversion of MEA was 63.4%, and with respect to the selectivity, EDA was 55.3%, PIP was 10.8%, DETA was 13.1%, AEEA was 10.4%, AEP was 1.3%, TETA was 1.9%, and TEPA was 1.0%. Further, the ratio of EDA/(PIP+AEEA) was 2.61.

EXAMPLE 65

4.96 g of nickel(II) nitrate hexahydrate, 0.11 g of yttrium(III) nitrate hexahydrate, 0.12 g of ytterbium(III) nitrate tetrahydrate, 0.067 g of dysprosium(III) nitrate hexahydrate and 0.11 g of palladium(II) nitrate were dissolved in 2.5 g of water, and 7.7 g of an activated alumina molded product (spherical, manufactured by Sumitomo Chemical Co., Ltd.) was immersed therein for one hour. Then, the product was evaporated to dryness by an evaporating dish on a hot water bath and then dried overnight at 120° C. After drying, it was calcined at 400° C. for one hour under a dry air stream of 200 ml/min. After calcination, it was again immersed in a solution having 4.96 g of nickel(II) nitrate hexahydrate, 0.11 g of yttrium(III) nitrate hexahydrate, 0.12 g of ytterbium(III) nitrate tetrahydrate, 0.067 g of dysprosium(III) nitrate hexahydrate and 0.11 g of palladium(II) nitrate dissolved in 2.5 g of water. Then, it was evaporated to dryness, dried, calcined and reduced in the same manner as in Example 61 to obtain Catalyst 58. The amount of Ni supported on this Catalyst 58 was 20% by weight, the atomic ratio of Ni/(Y+Yb+Dy) was 23.5, and the atomic ratio of Ni/Pd was 36.2. The X-ray diffraction of the catalyst was measured, whereby only the diffraction peak of nickel was ascertained, and the crystal size of nickel was 9.1 nm as obtained from the Scherrer's formula.

The reaction was conducted in the same manner as in Example 61 except that Catalyst 58 was used instead of Catalyst 55. As a result, the conversion of MEA was 64.7%, and with respect to the selectivity, EDA was 54.9%, PIP was 13.8%, DETA was 12.3%, AEEA was 7.3%, AEP was 1.6%, TETA was 1.8%, and TEPA was 1.1%. Further, the ratio of EDA/(PIP+AEEA) was 2.60.

EXAMPLES 66 to 80

A catalyst having Ni supported in an amount of 20% by weight was prepared in the same manner as for Catalyst 55 except that the M element and the carrier as identified in Table 7 were used instead of the yttrium(III) nitrate hexahydrate.

The reaction was conducted in the same manner as in Example 61 except that the catalyst as identified in Table 7 was used instead of Catalyst 55. The results of the reaction and the atomic ratio of the M element to Ni of the catalyst are shown in Table 8.

TABLE 7

| Example No. | Catalyst No. | M element | Reagent | Amount added (g) | Amount of carrier (g) |
|---|---|---|---|---|---|
| Example 66 | Catalyst 59 | Sc | Scandium(III) acetate | 0.49 | 7.6 |
| Example 67 | Catalyst 60 | La | Lanthanum(III) chloride heptahydrate | 0.40 | 7.5 |
| Example 68 | Catalyst 61 | Ce | Cerium(III) acetate | 0.11 | 7.7 |
| Example 69 | Catalyst 62 | Pr | Praseodymium(III) nitrate hexahydrate | 0.31 | 7.6 |
| Example 70 | Catalyst 63 | Nd | Neodymium(III) nitrate hexahydrate | 0.46 | 7.5 |
| Example 71 | Catalyst 64 | Sm | Samarium(III) nitrate hexahydrate | 0.30 | 7.6 |
| Example 72 | Catalyst 65 | Eu | Europium(III) chloride hexahydrate | 0.12 | 7.7 |
| Example 73 | Catalyst 66 | Gd | Gadolinium(III) nitrate hexahydrate | 0.29 | 7.6 |
| Example 74 | Catalyst 67 | Tb | Terbium(III) chloride hexahydrate | 0.23 | 7.6 |
| Example 75 | Catalyst 68 | Dy | Dysprosium(III) nitrate hexahydrate | 0.27 | 7.6 |
| Example 76 | Catalyst 69 | Ho | Holmium(III) acetate tetrahydrate | 0.13 | 7.7 |
| Example 77 | Catalyst 70 | Er | Erbium(III) nitrate hexahydrate | 0.28 | 7.6 |
| Example 78 | Catalyst 71 | Tm | Thulium(III) nitrate pentahydrate | 0.13 | 7.7 |
| Example 79 | Catalyst 72 | Yb | Ytterbium(III) nitrate tetrahydrate | 0.12 | 7.7 |
| Example 80 | Catalyst 73 | Lu | Lutetium(III) nitrate dihydrate | 0.34 | 7.5 |

TABLE 8

| Example No. | Catalyst No. | Atomic ratio of Ni/M | Conversion of MEA (%) | EDA (PIP + AEEA) |
| --- | --- | --- | --- | --- |
| Example 66 | Catalyst 59 | 7.6 | 59.6 | 2.54 |
| Example 67 | Catalyst 60 | 15.7 | 61.8 | 2.55 |
| Example 68 | Catalyst 61 | 47.6 | 60.3 | 2.61 |
| Example 69 | Catalyst 62 | 24.0 | 58.8 | 2.57 |
| Example 70 | Catalyst 63 | 16.3 | 60.9 | 2.56 |
| Example 71 | Catalyst 64 | 25.6 | 62.1 | 2.62 |
| Example 72 | Catalyst 65 | 51.8 | 58.7 | 2.57 |
| Example 73 | Catalyst 66 | 26.8 | 60.3 | 2.60 |
| Example 74 | Catalyst 67 | 27.0 | 59.1 | 2.56 |
| Example 75 | Catalyst 68 | 27.6 | 57.9 | 2.57 |
| Example 76 | Catalyst 69 | 56.1 | 58.2 | 2.54 |
| Example 77 | Catalyst 70 | 28.4 | 59.5 | 2.57 |
| Example 78 | Catalyst 71 | 57.4 | 60.8 | 2.55 |
| Example 79 | Catalyst 72 | 58.8 | 61.3 | 2.63 |
| Example 80 | Catalyst 73 | 19.8 | 60.4 | 2.58 |

EXAMPLE 81

Into a 200 ml stainless steel autoclave equipped with an electromagnetic stirrer, 60 g of EDA, and 30 g of MEA and 1 g of Catalyst 55 were charged and flushed with hydrogen. Then, hydrogen was introduced so that the hydrogen partial pressure became 20 kg/cm$^2$ at room temperature. Then, the rotational speed of the stirrer was adjusted to 500 rpm, and the temperature was raised to 200° C. The temperature was maintained at this level for 3 hours. After completion of the reaction, the reaction solution was analyzed by gas chromatography. As a result, the conversion of MEA was 25.9%, and the composition of products except for starting materials and formed water was 19.1% by weight of PIP, 62.0% by weight of DETA, 7.6% by weight of AEEA, 3.1% by weight of AEP and 7.8% by weight of TETA.

EXAMPLE 82

42.5 g of nickel(II) sulfate hexahydrate and 1.40 g of ytterbium(III) nitrate tetrahydrate were dissolved in 200 g of water, and 6 g of diatomaceous earth (manufactured by Johns-Manville Co.) was added. The mixture was maintained at 70° C. under stirring. To this mixture, a solution having 40 g of soda ash dissolved in 50 g of water under heating, was dropwise added over a period of 30 minutes, and the mixture was aged for one hour. After aging, the mixture was cooled to room temperature, and the precipitate was collected by filtration and washed with water. This precipitate was added to a solution having 2.42 g of palladium(II) nitrate dissolved in 30 g of water, to obtain a uniform slurry. Then, this slurry was evaporated to dryness on a hot water bath and then dried overnight at 120° C. After drying, it was calcined at 400° C. for one hour under a dry air stream of 200 ml/min. Then, it was reduced at 400° C. for 2 hours under a gas stream of 90 ml/min of hydrogen and 90 ml/min of nitrogen. At the time of calcination and reduction, the temperature raising rate was adjusted to be 10° C./min. The obtained catalyst was designated as Catalyst 74. The amount of Ni supported on this Catalyst 74 was 55.3% by weight, the atomic ratio of Ni/Yb was 50.2, and the atomic ratio of Ni/Pd was 15.4. The X-ray diffraction of the catalyst was measured, whereby only the diffraction peak of nickel was ascertained, and the crystal size of nickel was 7.0 nm as obtained from the Scherrer's formula.

Into a 200 ml stainless steel autoclave equipped with an electromagnetic stirrer, 30 g of MEA and 0.7 g of Catalyst 74 were charged and flushed with hydrogen. Then, 54 g of ammonia was added thereto, and hydrogen was introduced so that the hydrogen partial pressure became 20 kg/cm$^2$ at room temperature. Then, the rotational speed of the stirrer was adjusted to 1000 rpm, and the temperature was raised to 200° C. The temperature was maintained at this level for 3 hours. After completion of the reaction, the reaction solution was analyzed by gas chromatography. As a result, the conversion of MEA was 42.8%, and with respect to the selectivity, EDA was 64.0%, PIP was 6.7%, DETA was 9.8, AEEA was 9.0%, AEP was 0.3%, and TETA was 1.3%. Further, the ratio of EDA/(PIP+AEEA) was 4.08.

COMPARATIVE EXAMPLE 9

4.96 g of nickel(II) nitrate hexahydrate, 0.31 g of cerium(III) nitrate hexahydrate and 0.14 g of ammonium perrhenate were dissolved in 2.5 g of water, and 7.6 g of an activated alumina molded product (spherical, manufactured by Sumitomo Chemical Co., Ltd.) was immersed therein for one hour. The product was evaporated to dryness by an evaporating dish on a hot water bath and then dried overnight at 120° C. Then, it was calcined at 400° C. for one hour under a dry air stream of 200 ml/min. After calcination, it was again immersed in a solution having 4.96 g of nickel(II) nitrate hexahydrate, 0.31 g of cerium(III) nitrate hexahydrate and 0.14 g of ammonium perrhenate dissolved in 2.5 g of water. The product was evaporated to dryness by an evaporator on a hot water bath and then dried overnight at 120° C. Then, it was calcined at 400° C. for one hour under a dry air stream of 200 ml/min. After calcination, it was reduced at 500° C. for 2 hours under a gas stream of 30 ml/min of hydrogen and 30 ml/min of nitrogen. At the time of calcination and reduction, the temperature raising rate was adjusted to be 10° C./min. The obtained catalyst was designated as Comparative Catalyst 9. The amount of Ni supported on this Comparative Catalyst 9 was 20% by weight, the atomic ratio of Ni/Ce was 23.9, and the atomic ratio of Ni/Re was 31.7. The X-ray diffraction of the catalyst was measured, whereby only the diffraction peak of nickel was ascertained, and the crystal size of nickel was 8.3 nm as obtained from the Scherrer's formula.

The reaction was conducted in the same manner as in Example 1 except that Comparative Catalyst 9 was used instead of Catalyst 1. After completion of the reaction, the reaction solution was analyzed by gas chromatography. As a result, the conversion of MEA was 55.2%, and with respect to the selectivity, EDA was 53.7%, PIP was 11.3%, DETA was 9.5%, AEEA was 9.7%, AEP was 1.0%, TETA was 2.4%, and TEPA was 2.2%. Further, the ratio of EDA/(PIP+AEEA) was 2.56.

We claim:

1. A process for producing an ethylenamine, which comprises:

reacting ammonia and/or an ethylenamine with an ethanolamine in the presence of hydrogen and a catalyst comprising Ni, X and M elements, wherein X is Re, Ir, Pt or Pd and M is at least one rare earth element selected from the group consisting of scandium, yttrium, praseodymium, neodymium, samarium, europium, gadolinium, terbium, dysprosium, holmium, erbium, thulium, ytterbium and lutetium, thereby preparing an ethylenamine having an increased number of ethylene chains over the ammonia and/or ethylenamine staring material.

2. The process according to claim 1, wherein Ni in the catalyst is in the form of nickel metal or nickel oxide, X in the catalyst is in the form of metal or an oxide and M in the catalyst is in the form of metal or an oxide.

3. The process according to claim 1, wherein the atomic ratio of Ni/X is from 1 to 100, and the atomic ratio of Ni/M is from 0.5 to 100.

4. The process according to claim 1, wherein the reaction is conducted in a suspended bed system, and the catalyst is used in an amount of from 0.1 to 20% by weight relative to the total weight of the starting materials.

5. The process according to claim 1, wherein the ethanolamine is monoethanolamine, diethanolamine, triethanolamine, N-(2-aminoethyl)ethanolamine or N-(2-hydroxyethyl)piperazine.

6. The process according to claim 1, wherein the ethylenamine used as the starting material is ethylenediamine, diethylenetriamine, triethylenetetramine, tetraethylenepentamine, pentaethylenehexamine, piperazine, N-(2-aminoethyl)piperazine or triethylenediamine.

7. The process according to claim 1, wherein the reaction of ammonia with an ethanolamine is conducted at a molar ratio of the ammonia/the ethanolamine of from 1 to 50.

8. The process according to claim 1, wherein the reaction of an ethylenamine with an ethanolamine is conducted at a molar ratio of the ethylenamine/the ethanolamine of from 0.1 to 20.

9. The process according to claim 1, wherein the hydrogen is supplied at a molar ratio of the hydrogen/the ethanolamine of from 0.01 to 5.

10. The process according to claim 1, wherein the reaction is conducted at a temperature of from 110° to 290° C.

11. The process according to claim 1, wherein the reaction is conducted in a liquid phase.

* * * * *